(12) United States Patent
Bade et al.

(10) Patent No.: US 8,039,646 B2
(45) Date of Patent: Oct. 18, 2011

(54) PROCESS FOR PREPARING GLYCIDYLOXYALKYLTRIALKOXYSILANES

(75) Inventors: Stefan Bade, Michelbach le Haut (FR); Beate Seliger, Hamburg (DE); Norbert Schladerbeck, Kelkheim (DE); Joerg Sauer, Duelmen (DE)

(73) Assignee: Evonik Degussa GmbH, Essen (DE)

( * ) Notice: Subject to any disclaimer, the term of this patent is extended or adjusted under 35 U.S.C. 154(b) by 322 days.

(21) Appl. No.: 12/521,872

(22) PCT Filed: Dec. 20, 2007

(86) PCT No.: PCT/EP2007/064281
§ 371 (c)(1),
(2), (4) Date: Jul. 1, 2009

(87) PCT Pub. No.: WO2008/095570
PCT Pub. Date: Aug. 14, 2008

(65) Prior Publication Data
US 2010/0036146 A1     Feb. 11, 2010

(30) Foreign Application Priority Data
Feb. 9, 2007  (DE) .......................... 10 2007 007 185

(51) Int. Cl.
*C07D 303/22*    (2006.01)
(52) U.S. Cl. .......................... 549/215; 549/214; 556/479
(58) Field of Classification Search .................. 549/215, 549/214; 556/479
See application file for complete search history.

(56) References Cited

U.S. PATENT DOCUMENTS

| | | | |
|---|---|---|---|
| 4,966,981 A | 10/1990 | Takai et al. | |
| 5,616,762 A | 4/1997 | Kropfgans et al. | |
| 6,100,408 A | 8/2000 | Monkiewicz et al. | |
| 6,166,238 A | 12/2000 | Filipkowski et al. | |
| 6,402,961 B1 | 6/2002 | Bade et al. | |
| 2009/0068440 A1 | 3/2009 | Bub et al. | |

FOREIGN PATENT DOCUMENTS

| | | |
|---|---|---|
| EP | 0 288 286 | 10/1988 |
| JP | 2000 143679 | 5/2000 |
| WO | 01 51495 | 7/2001 |
| WO | 2008 017555 | 2/2008 |

OTHER PUBLICATIONS

Chernyshev, E. A. et al., "Hydrosilylation of Allyl Glycidyl Ether With Triethoxysilane", Russian Journal of General Chemistry, vol. 77, No. 1, pp. 55-61 (2007).
Sultanov, R. A. et al., "Hydrosilylation of Vinyl Glycidyl Ether", Zhurnal Obshchei Khimii, vol. 39, No. 2 (1969) (Abstract only).
U.S. Appl. No. 12/376,786, filed Feb. 9, 2009, Lang et al.

*Primary Examiner* — Elvis O Price
(74) *Attorney, Agent, or Firm* — Oblon, Spivak, McClelland, Maier & Neustadt, L.L.P.

(57) ABSTRACT

The present invention relates to a process for preparing glycidyloxy-alkylalkoxysilanes of the general formula (I) $(R'')O-C_nH_{2n}Si(R')_m(OR)_{3-m}$ (I) in which R and R' groups are each independently linear or branched alkyl groups having from 1 to 4 carbon atoms, n is 1, 2, 3, 4, 5, 6, 7 or 8 and m is 0, 1, 2 or 3, and R" is an $H_2C(O)CH-$ or $H_2C(O)CHCH_2-$ group, by reacting (i) a functionalized alkene of the general formula (II) $(R'')O-C_nH_{2n-1}$ (II) in which R" is an $H_2C(O)CH-$ or $H_2C(O)CHCH_2-$ group and n is 1, 2, 3, 4, 5, 6, 7 or 8 with (ii) at least one hydroalkoxy-silane of the general formula (III) $HSi(R')_m(OR)_{3-m}$ (III) in which R and R' groups are each independently linear or branched alkyl groups having from 1 to 4 carbon atoms and m is 0, 1, 2 or 3, in the presence (iii) of at least one homogeneous catalyst, (iv) of at least one solvent and/or of a diluent and (v) of at least one promoter.

17 Claims, No Drawings

PROCESS FOR PREPARING GLYCIDYLOXYALKYLTRIALKOXYSILANES

The invention relates to a process for preparing glycidyloxyalkylalkoxysilanes by hydrosilylation of an olefin glycidyl ether in the presence of a catalyst.

Epoxy-functional silanes are important industrial intermediates or end products in organosilane chemistry. They are used as bonding agents in composites, e.g. in the surface coatings and fiberglass industries, in foundry technology and in the adhesive industry; said compounds also play an important role in the coating of optical glasses.

The preparation of glycidyloxyalkylalkoxysilanes is carried out, for example, by reacting a trialkoxysilane bearing a hydrogen atom with allyl glycidyl ether in the presence of a hydrosilylation catalyst and can be described by the following general reaction equation:

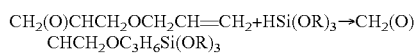
$$CH_2(O)CHCH_2OCH_2CH{=}CH_2 + HSi(OR)_3 \rightarrow CH_2(O)CHCH_2OC_3H_6Si(OR)_3$$

where R=alkyl, e.g. methyl, ethyl, propyl. Thus, when R=methyl, the preparation of 3-glycidyloxypropyltrimethoxysilane is described and when R=ethyl, the preparation of 3-glycidyloxypropyltriethoxysilane is described. By-products formed here are isomers, $CH_2(O)CHCH_2OCH_2CH(Si(OR)_3)CH_3$ and a corresponding 8-membered heterocycle, also glycidyloxytrialkoxysilane, propyltrialkoxysilane, propenyl glycidyl ether and tetraalkoxysilane, and also high-boiling components. The compounds which are difficult to separate off by distillation, isomeric glycidylalkoxypropyltrialkoxysilane and the 8-membered heterocycle in particular, require a large number of theoretical plates in a distillation column and long distillation times. The formation of propenyl glycidyl ether and the formation of tetraalkoxysilane represent large selectivity losses.

Hydrosilylation reactions of H-silanes with compounds containing a C=C double bond are carried out either batchwise or continuously, with the hydrosilylation reaction generally being catalyzed by noble metals. The preparation of 3-glycidyloxypropyltrialkoxysilanes is usually carried out by homogeneous catalysis using a Speier catalyst, $H_2PtCl_6$, or a Karstedt catalyst, divinyltetramethyldisiloxane-Pt (EP 0 277 023, EP 0 288 286, JP 128763 and DE 2 159 991), but can also be carried out by heterogeneous catalyst using noble metals (EP 0 548 974, U.S. Pat. No. 4,736,049).

If the hydrosilylation of allyl glycidyl ether with trimethoxysilane is carried out in the presence of a homogeneous Pt catalyst, it is observed that a not negligible proportion of the allyl glycidyl ether used is isomerized and is thus no longer available for the hydrosilylation. This generally causes considerable selectivity losses.

A further disadvantage of the homogeneous catalysts used hitherto is the formation of colloidal Pt, which likewise leads to increased by-product formation. The formation of colloidal Pt is observed particularly in the case of homogeneous catalysts of the Karstedt type. Apart from a reduction in the target product selectivity, there is isomerization of the olefin used which after isomerization is no longer available for the hydrosilylation.

EP 0 985 675 discloses the use of an acid as promoter in the hydrosilylation of an olefin for the preparation of alkylsilanes.

SU 415268 teaches the preparation of aminoalkylsilanes by hydrosilylation of allylamine, with this reaction also being carried out in the presence of a catalyst and with addition of an acid as promoter.

It is generally known that an oxirane ring generally opens under the action of an acid and is thus a very reactive species. The opening of the oxirane ring here occurs both by means of acid catalysis and also by means of any other nucleophiles. (S. Hauptmann, "Organische Chemie", 1st edition 1985, VEB Verlag für Grundstoffindustrie, Leipzig, pages 558ff).

It was an object of the present invention to provide a further, improved process for preparing glycidyloxyalkylalkoxysilanes. In particular, it was an intention to reduce the abovementioned disadvantages and the economic losses associated therewith.

The object is achieved according to the invention by the features in the claims.

Thus, it has surprisingly been found that homogeneous Pt catalysts, in particular hexachloroplatinic acid and a Karstedt catalyst, in the presence of an acid promoter, in particular a monocarboxylic or dicarboxylic acid, do not cause epoxide ring opening either of the allyl glycidyl ether or of the product glycidyloxyalkylalkoxysilane. Thus, the homogeneous catalyst can advantageously be used, in particular, in combination with the promoter and a suitable solvent or diluent or a corresponding mixture, with the respective target product being particularly advantageously used as solvent or diluent. In addition, the selectivity can be increased in an advantageous manner by the present promoter process. Thus, the formation of colloidal Pt and by-product formation can advantageously be reduced by means of the teaching according to the invention. In particular, the proportion of isomerized product, of isomerized olefin and of tetraalkoxysilane can be significantly reduced. This effect occurs in the process of the invention especially when using Speier catalysts or Karstedt catalysts in said combination with a promoter. Particularly advantageously, the product selectivity is increased and the formation of isomers and of by-products is suppressed when an excess of the olefinic component over the hydrogentrialkoxysilane is used. Thus, selectivities to the target product of >87% together with virtually quantitative conversion (>98%) of the trialkoxysilane component could be obtained by means of the present invention.

It has likewise been found that despite adiabatic reaction conditions in the reactor and the associated high temperatures, the promoter displays its selectivity-increasing action during the course of the reaction and, despite the high temperatures, the oxirane ring is particularly advantageously retained even though the promoter has acid activity.

Furthermore, it has surprisingly been found that the water content in the promoter does not have a significant adverse effect on the selectivity. The adiabatic mode of operation of the reactor leads to particularly advantageous short residence times and to a reduced proportion of by-products.

The present invention accordingly provides a process for preparing glycidyloxyalkylalkoxysilanes of the general formula (I)

$$(R'')O-C_nH_{2n}Si(R')_m(OR)_{3-m} \qquad (I),$$

where groups R and R' are each, independently of one another, a linear or branched alkyl group having from 1 to 4 carbon atoms, preferably methyl, ethyl or propyl, n is 1, 2, 3, 4, 5, 6, 7 or 8 and m is 0, 1, 2 or 3 and R" is an $H_2C(O)CH-$ or $H_2C(O)CHCH_2-$ group,
which comprises reacting
(i) a functionalized alkene of the general formula (II)

$$(R'')O-C_nH_{2n-1} \qquad (II),$$

where R" is an $H_2C(O)CH-$ or $H_2C(O)CHCH_2-$ group and n is 1, 2, 3, 4, 5, 6, 7 or 8,
with
(ii) at least one hydrogenalkoxysilane of the general formula (III)

$$HSi(R')_m(OR)_{3-m} \qquad (III),$$

where groups R and R' are each, independently of one another, a linear or branched alkyl group having from 1 to 4 carbon atoms and m is 0, 1, 2 or 3,
in the presence of
(iii) at least one homogeneous catalyst,
(iv) at least one solvent and/or at least one diluent and
(v) at least one promoter.

In the process of the invention, allyl glycidyl ether is preferably used as olefin component (i).

Preference is given to using trimethoxysilane or triethoxysilane as hydrogenalkoxysilane (ii) in the process of the invention.

Here, the components (i) olefin and (ii) hydrogenalkoxysilane are advantageously used in a molar ratio of 1.8-1.0:1.0, preferably 1.3-1.1:1.0.

Furthermore, the hydrosilylation in the process of the invention is carried out in the presence of (iii) at least one homogeneous catalyst from the group consisting of Speier and Karstedt catalysts.

A person skilled in the art will generally understand a Speier catalyst as can be used in the process of the invention as hexachloroplatinic acid or hexachloroplatinic acid dissolved in isopropanol. However, other solvents such as acetone or methanol, or solvent mixtures, will also be known to a person skilled in the art for this catalyst system.

Karstedt catalysts are soluble Pt(0) complex catalysts as are described, for example, in U.S. Pat. No. 3,775,452, DE-A 19 41 411 or in Marciniec, B., "Comprehensive Handbook of Hydrosilylation", Pergamon Press, New York (1992). In particular, Pt(0)-divinyltetramethyldisiloxane is used in the process of the invention, with the complex generally being dissolved in the complexing agent and being present in the form of a concentrate. The complex catalyst or the concentrate of Pt(0)-divinyltetramethyldisiloxane in divinyltetramethyldisiloxane as catalyst system can also advantageously be used as a solution in xylene and/or the target product of the present process, i.e. preferably in 3-glycidyloxypropyltrimethoxysilane or 3-glycidyloxypropyltriethoxysilane. In addition, the promoter component (v) can advantageously be added to a catalyst composition which can be obtained in this way.

Thus, the catalyst (iii) is preferably used in at least one solvent, in particular in divinyltetramethyldisiloxane, and/or at least one diluent, preferably diluted in the hydrosilylation product, i.e. the target compound, in particular 3-glycidyloxypropyltrimethoxysilane or 3-glycidyloxypropyltriethoxysilane, in the process of the invention. Here, the solvent or diluent used can simultaneously serve as diluent for the reaction mixture present in the process.

The catalyst (iii) (based on the metal) is advantageously used in a molar ratio to the olefin component (i) of from 1:1 000 000 to 1:25 000, preferably from 1:500 000 to 1:100 000.

Thus, the reaction (hydrosilylation) in the process of the invention is advantageously carried out in the presence of (iv) at least one solvent and/or at least one diluent from the group consisting of paraffins, toluene, xylene, the organic complexing agent of the catalysts, for example divinyltetramethyldisiloxane, the hydrosilylation products (target product) or a mixture of at least two of the abovementioned materials. Thus, solvent and/or diluent are preferably used in a mass ratio to catalyst (calculated as Pt metal) of 100 000-10:1, particularly preferably 10 000-50:1, in particular 5000-100:1. In this way, the starting materials can be introduced largely uniformly and thus mixed in an advantageous manner in the starting mixture and during the further course of the process.

Furthermore, the reaction is advantageously carried out in the presence of (v) at least one acid promoter from the group consisting of monocarboxylic and dicarboxylic acids, preferably monoacids such as formic acid, acetic acid and propionic acid, and other H-acidic compounds, for example phenol or phenol derivatives. The water content in the promoters can be from 0 to 3000 ppm by weight.

The catalyst (iii) and the promoter (v) are preferably used in a molar ratio (catalyst based on metal) of from 1:250 to 1:25 000, preferably from 1:1000 to 1:5000, in the process of the invention.

In particular, the catalyst (iii) and the promoter (v) are used together in (iv) at least one solvent and/or at least one diluent, preferably diluted in the hydrosilylation product, in the process of the invention. Preference is given to a mass ratio of solvent and/or diluent to promoter of 1000-0.001:1, particularly preferably 100-0.01:1, in particular 10-0.1:1.

To carry out the process of the invention, the components (i), (ii), (iii), (iv) and (v) are advantageously fed into a tangential mixer at ambient temperature, preferably from 0 to 40° C., mixed and fed as mixture directly into a reactor. The components (iii), (iv) and (v) can be used as mixture or solution for the metered addition.

The reactor is particularly advantageously configured as an adiabatically operated tube reactor, bubble column reactor or stirred or unstirred tank reactor. The reactor is appropriately heatable and coolable, so that the reactor can be preheated to start up the process and the heating is either stopped or adjusted to a desired operating temperature as soon as the exothermic reaction has commenced. In particular, the reactor is operated under level control and the reaction mixture is mixed by rising gas bubbles, as in a bubble column, so that the reactor system can be operated with a high level of backmixing. The advantage of this reactor system is that no additional conditioning of the reactor is required for start-up. Furthermore, a prereactor and internals in the reactor, e.g. packing elements, can advantageously be dispensed with in the present process.

Thus, the process of the invention is preferably carried out using a tube reactor, a bubble column reactor or a stirred or unstirred tank reactor.

Suitable reactor materials are generally all stainless steels, and preference is given to using Inconel, Hastelloy C4, nickel, enamel on metal, i.e. especially reactors enameled in the reaction region, or glass, for example an appropriately heat-resistant glass or fused silica. In particular, a tube reactor having a diameter in the range from 5 to 20 cm, preferably 10 cm, and a length of from 100 to 400 cm, is used for the reaction according to the invention. A plurality of reactors can be connected in parallel or in series.

In the process of the invention, the reaction in the reactor is preferably carried out at a reaction temperature in the range from 40 to 200° C., particularly preferably from 60 to 160° C., and a pressure of from 0.5 to 20 bar abs., in particular ambient pressure, i.e. 1 bar, and a space velocity of from 3 to 30 [1/h], in particular from 5 to 10 [1/h] (figures at STP). The average residence time of the reaction mixture in the reactor is preferably from 1 to 20 minutes, particularly preferably from 3 to 9 minutes, in particular from 5 to 8 minutes.

The reaction product obtained in this way is generally worked up. For this purpose, the reaction product leaving the reactor is collected in an appropriate manner in a reservoir and subsequently passed to a distillation. In the distillation, the olefin component used in excess and any solvent used are appropriately separated off and can advantageously be recycled. In addition, the target or end product is obtained in an advantageous manner; in particular, 3-gylcidyloxypropyltrimethoxysilane or 3-glycidyloxypropyltriethoxysilane is obtained in an advantageous manner.

The process of the invention, in particular the steps of mixing and introduction of the starting components, reaction (hydrosilylation) and work-up, can be carried out batchwise or continuously.

In general, the process of the invention is carried out as follows:

the functionalized alkene, the hydrogenalkoxysilane, the homogeneous catalyst in its solvent, the diluent and the promoter are generally fed in ideally mixed form and continuously to the reactor via a mixing stage. The starting components (i) to (v) are in this way appropriately introduced into a tangential mixer, mixed and fed as reaction mixture to the reactor system which is at operating temperature. For this purpose, the catalyst or the catalyst system can be mixed with a solvent, a diluent or a mixture of solvent and diluent and also the promoter and introduced as a mixture. However, it is also possible to mix the catalyst with solvent or diluent and feed the mixture obtained in this way into the mixing stage. Here, the promoter can be introduced separately from the catalyst/solvent or diluent mixture into the mixing stage. Furthermore, the promoter can be introduced as a mixture with solvent or diluent. After commencement of the reaction (hydrosilylation) in the reactor, the external energy input can advantageously be stopped and the heat of reaction can be utilized for internal heating of the reaction mixture. The reactor is preferably operated continuously and with a high level of backmixing and a short residence time. In this way, a high conversion of 98-100% of the trialkoxysilane component is obtained in a particularly advantageous way in the process of the invention.

The product mixture obtained in the reaction (hydrosilylation) can subsequently be worked up by means of distillation.

Here, the distillation can be carried out under reduced pressure, for example in a column system, a thin film evaporator or short path evaporator. Olefin component used in excess and separated off in the work-up and also solvent or diluent and promoter separated off here can be recycled. The target product is generally obtained in the bottoms and can be subjected to an additional pure distillation as part of the work-up.

Thus, the process of the invention displays, especially as a result of its comparatively high selectivity, significantly improved economics. The increase in the selectivity is achieved, according to the invention, by use of the specially selected catalyst systems in combination with at least one promoter and a solvent or diluent, which can advantageously suppress by-product formation, in particular of isomerized olefin, isomerized target product and tetraalkoxysilane. The high target product selectivity at virtually quantitative conversion of the trialkoxysilane component is particularly advantageous.

The present invention is illustrated by the following example, without the subject matter of the invention being restricted thereto.

EXAMPLE

In the example, allyl glycidyl ether was reacted with trimethoxysilane to form 3-glycidyloxypropyltrimethoxysilane. The reaction was carried out continuously by feeding the raw materials (allyl glycidyl ether: 9.6 kg/h and trimethoxysilane: 8 kg/h) together with the Pt Karstedt catalyst in the presence of acetic acid (0.05% by weight, based on the total mass of reactants) into a tube reactor. The concentration of the catalyst based on metallic platinum was 2 ppm. The Pt Karstedt catalyst was dissolved in 3-glycidyloxypropyltrimethoxysilane. The reaction temperature was about 160° C. The reaction was carried out using an excess of allyl glycidyl ether (molar ratio of allyl glycidyl ether:trimethoxysilane=1.28:1). The reaction mixture formed was composed of:

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 0.2 | 0.4 | 0.4 | 6.4 | 3 | 0.3 | 0.1 | 87.3 | 1.9 |

TMOS = trimethoxysilane
DYN M = tetramethoxysilane
AGE = allyl glycidyl ether
cis-iso-AGE = cis-propenyl glycidyl ether
trans-iso-AGE = trans-propenyl glycidyl ether
iso-GLYMO = 2-glycidyloxy-1-methylethyltrimethoxysilane
cyclo-GLYMO = 1-dimethoxysila-2,5-dioxa-3-methoxymethylcyclooctane
GLYMO = 3-glycidyloxypropyltrimethoxysilane
HB = high boilers The composition of the product mixture was determined by means of gas chromatography.

When the above-described process is carried out without the use of acetic acid as promoter, the following reaction composition is obtained.

| TMOS [%] | DYN M [%] | AGE [%] | cis-iso-AGE [%] | trans-iso-AGE [%] | iso-GLYMO [%] | cyclo-GLYMO [%] | GLYMO [%] | HB [%] |
|---|---|---|---|---|---|---|---|---|
| 0.3 | 1.15 | 1.7 | 6.35 | 6.35 | 1.1 | 0.15 | 81 | 1.9 |

The advantages of the homogeneous PT catalyst in the presence of organic acid in combination with the use of the target product as solvent or diluent are increased selectivity to the target product, in particular a reduction in the proportion of iso product and cyclo product, and the suppression of the isomerization of the olefinic compound used.

The reduced by-product formation also makes the crude product easier to distil and leads to an increase in quality, i.e. a low number of theoretical plates can be used and shorter distillation times for the distillation batch can be employed when iso and cyclo product are present in smaller amounts. The purity of the target product 3-glycidyloxypropyltrimethoxysilane can also be increased.

The invention claimed is:

1. A process for preparing glycidyloxyalkylalkoxysilanes of the general formula (I)

$$(R'')O\text{—}C_nH_{2n}Si(R')_m(OR)_{3-m} \quad (I),$$

where groups R and R' are each, independently of one another, a linear or branched alkyl group having from 1 to 4 carbon atoms, n is 1, 2, 3, 4, 5, 6, 7 or 8 and m is 0, 1, 2 or 3 and R'' is an $H_2C(O)CH\text{—}$ or $H_2C(O)CHCH_2\text{—}$ group, which comprises reacting (i) a functionalized alkene of the general formula (II)

$$(R'')O\text{—}C_nH_{2n-1} \quad (II),$$

where R'' is an $H_2C(O)CH\text{—}$ or $H_2C(O)CHCH_2\text{—}$ group and n is 1, 2, 3, 4, 5, 6, 7 or 8, with (ii) at least one hydrogenalkoxysilane of the general formula (III)

$$HSi(R')_m(OR)_{3-m} \quad (III),$$

where groups R and R' are each, independently of one another, a linear or branched alkyl group having from 1 to 4 carbon atoms and m is 0, 1, 2 or 3, in the presence of (iii) at least one homogeneous catalyst,
(iv) at least one solvent and/or at least one diluent and
(v) at least one promoter.

2. The process as claimed in claim 1, wherein allyl glycidyl ether is used as functional olefin component (i).

3. The process as claimed in claim 1, wherein trimethoxysilane or triethoxysilane is used as hydrogenalkoxysilane (ii).

4. The process as claimed in claim 1, wherein the components (i) and (ii) are used in a molar ratio of 1.8-1.0:1.0.

5. The process as claimed in claim 1, wherein the hydrosilylation is carried out in the presence of (iii) at least one homogeneous catalyst selected from the group consisting of Speier and Karstedt catalysts.

6. The process as claimed in claim 1, wherein the catalyst (iii) is diluted in the hydrosilylation product.

7. The process as claimed in claim 1, wherein the catalyst (iii) is used in a molar ratio to the olefin component (i) of from 1:1 000 000 to 1:25 000.

8. The process as claimed in claim 1, wherein the reaction is carried out in the presence of (iv) at least one solvent and/or at least one diluent selected from the group consisting of paraffins, toluene, xylene, the organic complexing agents of the catalysts, the hydrosilylation products and a mixture of at least two of said materials.

9. The process as claimed in claim 1, wherein the reaction is carried out in the presence of (v) at least one acid promoter selected from the group consisting of monocarboxylic and dicarboxylic acids and other H-acidic compounds.

10. The process as claimed in claim 1, wherein the catalyst (iii) and the promoter (v) are used in a molar ratio of from 1:250 to 1:25 000.

11. The process as claimed in claim 1, wherein the catalyst (iii) and the promoter (v) are used together diluted in the hydrosilylation product.

12. The process as claimed in claim 1, wherein the components (i), (ii), (iii), (iv) and (v) are introduced into a tangential mixer, mixed and fed to a reactor.

13. The process as claimed in claim 1, wherein the reaction in the reactor is carried out at a reaction temperature in the range from 40 to 200° C., a pressure of from 0.5 to 20 bar and a space velocity of from 3 to 30 [1/h].

14. The process as claimed in claim 1, wherein the reaction is carried out in a tube reactor, a bubble column reactor or a stirred or unstirred tank reactor.

15. The process as claimed in claim 1, wherein the reaction product is worked up.

16. The process as claimed in claim 1, wherein reaction and work-up are carried out batchwise or continuously.

17. The process as claimed in claim 1, wherein a product selected from the group consisting of 3-glycidyloxypropyltrimethoxysilane and 3-glycidyloxypropyltriethoxysilane is obtained.

* * * * *